United States Patent
Augoyard et al.

(10) Patent No.: US 8,475,456 B2
(45) Date of Patent: Jul. 2, 2013

(54) INTRAMEDULLAR OSTEOSYNTHETIC DEVICE OF TWO BONE PARTS, IN PARTICULAR OF THE HAND AND/OR FOOT

(75) Inventors: Marc Augoyard, Tassin la Demi Lune (FR); Jacques Peyrot, Tassin la Demi Lune (FR); Tristan Meusnier, Saint-Etienne (FR); Bernard Prandi, Rennes (FR)

(73) Assignee: Memometal Technologies (FR)

( * ) Notice: Subject to any disclaimer, the term of this patent is extended or adjusted under 35 U.S.C. 154(b) by 717 days.

(21) Appl. No.: 11/911,405

(22) PCT Filed: Apr. 12, 2006

(86) PCT No.: PCT/FR2006/050345
§ 371 (c)(1),
(2), (4) Date: Mar. 17, 2008

(87) PCT Pub. No.: WO2006/109004
PCT Pub. Date: Oct. 19, 2006

(65) Prior Publication Data
US 2008/0177262 A1 Jul. 24, 2008

(30) Foreign Application Priority Data
Apr. 14, 2005 (FR) ...................................... 05 50957

(51) Int. Cl.
*A61B 17/58* (2006.01)
(52) U.S. Cl.
USPC ................................ 606/62; 606/75; 606/331
(58) Field of Classification Search
USPC ............... 132/283, 276, 281; 606/62–28, 80, 606/75, 78, 151, 157, 280, 283, 286, 296–299, 606/911, 913, 327, 62–68; 623/21.11, 21.15, 623/21.18, 21.19, 23.39, 23.41
See application file for complete search history.

(56) References Cited

U.S. PATENT DOCUMENTS

| 3,462,765 A | 8/1969 | Swanson |
| 3,466,669 A | 9/1969 | Flatt |

(Continued)

FOREIGN PATENT DOCUMENTS

| EP | 1300122 A | 4/2003 |
| EP | 1923012 A1 | 5/2008 |

(Continued)

OTHER PUBLICATIONS

International Search Report for PCT/FR2006/050345.

(Continued)

*Primary Examiner* — Kevin T Truong
*Assistant Examiner* — Christian Sevilla
(74) *Attorney, Agent, or Firm* — Lerner, David, Littenberg, Krumholz & Mentlik, LLP

(57) ABSTRACT

An intramedullar osteosynthetic device includes a body with an elongated shape and a flat cross-section having, in succession, from one of its ends, a first fixation zone cooperating with one of the bone parts to be immobilized, a median zone suitable for withstanding the shear and bending stresses, and a second fixation zone in the other bone part to be immobilized. Each of the fixation zones is made from a material suitable for enabling their deformation by thermal action (tepid memory) or mechanical action (superelasticity), to permit an introduction into the bone parts without pulpar approach, followed by a fixation in the bone parts, while avoiding any rotational movement, withstanding the tensile stresses, and maintaining a compressive force. At least one of the fixation zones has two tabs or fins and which are separable under the effect of the deformation.

24 Claims, 2 Drawing Sheets

U.S. PATENT DOCUMENTS

| | | | |
|---|---|---|---|
| 3,593,342 A | 7/1971 | Niebauer et al. | |
| 3,681,786 A | 8/1972 | Lynch | |
| 3,739,403 A | 6/1973 | Nicolle | |
| 3,824,631 A | 7/1974 | Burstein | |
| D243,716 S | 3/1977 | Treace et al. | |
| 4,204,284 A | 5/1980 | Koeneman | |
| 4,276,660 A | 7/1981 | Laure | |
| 4,364,382 A | 12/1982 | Mennen | |
| D277,509 S | 2/1985 | Lawrence et al. | |
| D277,784 S | 2/1985 | Sgarlato et al. | |
| D284,099 S | 6/1986 | Laporta et al. | |
| 4,634,382 A | 1/1987 | Kusano et al. | |
| D291,731 S | 9/1987 | Aikins | |
| 4,759,768 A | 7/1988 | Hermann et al. | |
| 4,955,916 A | 9/1990 | Carignan et al. | |
| 4,969,909 A * | 11/1990 | Barouk | 623/21.15 |
| 5,047,059 A | 9/1991 | Saffar | |
| 5,092,896 A | 3/1992 | Meuli et al. | |
| 5,133,761 A | 7/1992 | Krouskop | |
| 5,179,915 A * | 1/1993 | Cohen et al. | 606/62 |
| 5,190,546 A | 3/1993 | Jervis | |
| 5,207,712 A | 5/1993 | Cohen | |
| 5,326,364 A | 7/1994 | Clift, Jr. et al. | |
| 5,405,400 A | 4/1995 | Linscheid et al. | |
| 5,405,401 A | 4/1995 | Lippincott, III et al. | |
| 5,425,777 A | 6/1995 | Sarkisian | |
| 5,480,447 A | 1/1996 | Skiba | |
| 5,507,822 A | 4/1996 | Bouchon et al. | |
| 5,522,903 A | 6/1996 | Sokolow et al. | |
| 5,554,157 A | 9/1996 | Errico et al. | |
| 5,634,925 A | 6/1997 | Urbanski | |
| 5,674,297 A | 10/1997 | Lane et al. | |
| 5,702,472 A | 12/1997 | Huebner | |
| 5,725,585 A | 3/1998 | Zobel | |
| 5,782,927 A | 7/1998 | Klawitter et al. | |
| 5,876,434 A | 3/1999 | Flomenblit et al. | |
| 5,882,444 A | 3/1999 | Flomenblit et al. | |
| 5,951,288 A | 9/1999 | Sawa | |
| 5,958,159 A | 9/1999 | Prandi | |
| 5,984,970 A | 11/1999 | Bramlet | |
| 6,011,497 A | 1/2000 | Tsang et al. | |
| 6,017,366 A | 1/2000 | Berman | |
| 6,146,387 A * | 11/2000 | Trott et al. | 606/104 |
| 6,197,037 B1 * | 3/2001 | Hair | 606/151 |
| 6,200,330 B1 | 3/2001 | Benderev et al. | |
| 6,248,109 B1 * | 6/2001 | Stoffella | 606/75 |
| 6,319,284 B1 | 11/2001 | Rushdy et al. | |
| 6,352,560 B1 | 3/2002 | Poeschmann et al. | |
| 6,383,223 B1 | 5/2002 | Baehler et al. | |
| 6,386,877 B1 | 5/2002 | Sutter | |
| 6,423,097 B2 | 7/2002 | Rauscher | |
| 6,428,634 B1 | 8/2002 | Besselink et al. | |
| 6,454,808 B1 | 9/2002 | Masada | |
| 6,475,242 B1 | 11/2002 | Bramlet | |
| 6,699,247 B2 | 3/2004 | Zuckerman et al. | |
| 6,699,292 B2 | 3/2004 | Ogilvie et al. | |
| 6,706,045 B2 | 3/2004 | Lin et al. | |
| 6,811,568 B2 | 11/2004 | Minamikawa | |
| 6,869,449 B2 | 3/2005 | Ball et al. | |
| 7,037,342 B2 | 5/2006 | Nilsson et al. | |
| 7,041,106 B1 | 5/2006 | Carver et al. | |
| 7,182,787 B2 | 2/2007 | Hassler et al. | |
| 7,240,677 B2 | 7/2007 | Fox | |
| 7,291,175 B1 | 11/2007 | Gordon | |
| 7,588,603 B2 | 9/2009 | Leonard | |
| 7,780,737 B2 | 8/2010 | Bonnard et al. | |
| 7,837,738 B2 | 11/2010 | Reigstad et al. | |
| 7,842,091 B2 | 11/2010 | Johnstone et al. | |
| 2001/0025199 A1 | 9/2001 | Rauscher | |
| 2002/0019636 A1 | 2/2002 | Ogilvie et al. | |
| 2002/0055785 A1 | 5/2002 | Harris | |
| 2002/0065561 A1 | 5/2002 | Ogilvie et al. | |
| 2002/0068939 A1 * | 6/2002 | Levy et al. | 606/63 |
| 2002/0082705 A1 | 6/2002 | Bouman et al. | |
| 2003/0040805 A1 | 2/2003 | Minamikawa | |
| 2003/0069645 A1 | 4/2003 | Ball et al. | |
| 2004/0093081 A1 | 5/2004 | Nilsson et al. | |
| 2004/0102853 A1 | 5/2004 | Boumann et al. | |
| 2004/0138756 A1 | 7/2004 | Reeder | |
| 2004/0220678 A1 | 11/2004 | Chow et al. | |
| 2005/0119757 A1 | 6/2005 | Hassler et al. | |
| 2005/0251265 A1 | 11/2005 | Calandruccio et al. | |
| 2005/0283159 A1 * | 12/2005 | Amara | 606/75 |
| 2006/0052725 A1 | 3/2006 | Santilli | |
| 2006/0052878 A1 | 3/2006 | Schmieding | |
| 2006/0074492 A1 | 4/2006 | Frey | |
| 2006/0084998 A1 | 4/2006 | Levy et al. | |
| 2006/0247787 A1 | 11/2006 | Rydell et al. | |
| 2007/0038303 A1 | 2/2007 | Myerson et al. | |
| 2007/0123993 A1 | 5/2007 | Hassler et al. | |
| 2007/0142920 A1 | 6/2007 | Niemi | |
| 2007/0185584 A1 | 8/2007 | Kaufmann et al. | |
| 2007/0213831 A1 | 9/2007 | de Cubber | |
| 2007/0239158 A1 | 10/2007 | Trieu et al. | |
| 2008/0039949 A1 | 2/2008 | Meesenburg et al. | |
| 2008/0154385 A1 | 6/2008 | Trail et al. | |
| 2008/0195219 A1 | 8/2008 | Wiley et al. | |
| 2008/0221697 A1 | 9/2008 | Graser | |
| 2008/0221698 A1 | 9/2008 | Berger | |
| 2008/0269908 A1 | 10/2008 | Warburton | |
| 2009/0254189 A1 | 10/2009 | Scheker | |
| 2009/0254190 A1 | 10/2009 | Gannoe et al. | |
| 2010/0010637 A1 | 1/2010 | Pequignot | |
| 2010/0016982 A1 | 1/2010 | Solomons | |
| 2010/0057214 A1 | 3/2010 | Graham et al. | |
| 2010/0121390 A1 | 5/2010 | Kleinman | |
| 2010/0131014 A1 | 5/2010 | Peyrot | |
| 2010/0131072 A1 | 5/2010 | Schulte | |
| 2010/0161068 A1 | 6/2010 | Lindner et al. | |
| 2010/0185295 A1 | 7/2010 | Emmanuel | |
| 2010/0249942 A1 | 9/2010 | Goswami et al. | |
| 2010/0256770 A1 | 10/2010 | Hakansson et al. | |
| 2010/0262254 A1 | 10/2010 | Lawrence et al. | |
| 2011/0004317 A1 | 1/2011 | Hacking et al. | |

FOREIGN PATENT DOCUMENTS

| | | |
|---|---|---|
| FR | 2725126 A1 | 4/1996 |
| FR | 2783702 A | 3/2000 |
| FR | 2787313 A | 6/2000 |
| FR | 2794019 A | 12/2000 |
| FR | 2846545 A | 5/2004 |
| FR | 2884406 | 10/2006 |
| GB | 2119655 A | 11/1983 |
| GB | 2430625 A | 4/2007 |
| JP | 60145133 A | 7/1985 |
| JP | 7303662 A | 11/1995 |
| JP | 2004535249 A | 11/2004 |
| JP | 2007530194 A | 11/2007 |
| WO | 2005/063149 A | 7/2005 |
| WO | 2005/104961 A | 10/2005 |
| WO | 2006109004 A1 | 10/2006 |

OTHER PUBLICATIONS

International Search Report for PCT/FR2008/050453 dated Nov. 4, 2008.

* cited by examiner

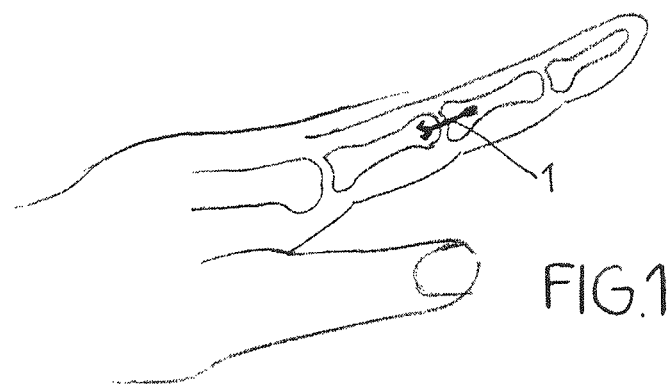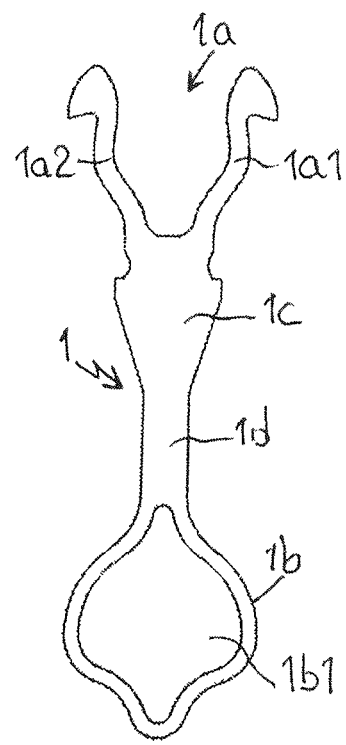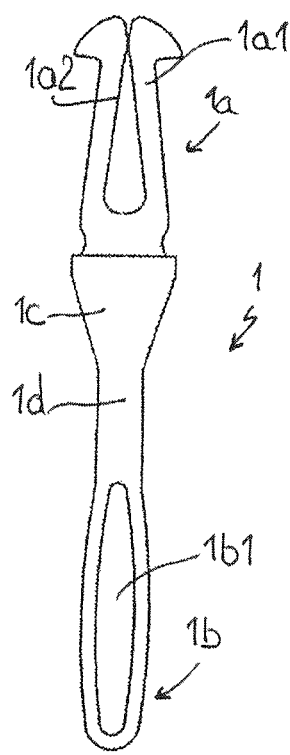

INTRAMEDULLAR OSTEOSYNTHETIC DEVICE OF TWO BONE PARTS, IN PARTICULAR OF THE HAND AND/OR FOOT

CROSS REFERENCE TO RELATED APPLICATIONS

This application is the US national phase of PCT application PCT/FR2006/050345, filed 12 Apr. 2006, published 19 Oct. 2006 as WO2006/109004, and claiming the priority of PCT patent application PCT/FR2006/050345 itself filed 12 Apr. 2006, whose entire disclosures are herewith incorporated by reference.

FIELD OF THE INVENTION

The invention relates to the technical field of orthopaedic implants, particularly for arthrodeses and osteosyntheses.

It may be recalled that the object of an arthrodesis is to obtain very good stability both primary and secondary, and to place, or to maintain, in compression, two bone parts or bone fragments that should be consolidated. Stability is a critical factor for obtaining consolidation, while minimizing the attendant problems such as pain, swelling, etc. The compressive action serves to consolidate the osteotomy more rapidly in the position selected by the surgeon during the operation.

Various technical solutions have been proposed for carrying out an arthrodesis, particularly in the foot, the hand, the wrist, etc. Mention can be made, for example, of basic staples without shape memory which do not produce a compression, as opposed to memory staples which serve to place the two bone parts to be consolidated in compression, which corresponds to the objective.

However, to obtain satisfactory stability, it is necessary to place two, or even three staples, in different planes. This increases the dimensions considerably, thereby limiting applications (metacarpo-phalangeal joint, for example).

Extramedullary plates and screws have also been proposed, requiring an alternatively large dimension. In this respect, their miniaturization is difficult to conceive, because this could raise problems of strength and stiffness. Some types of screws can be used in intramedullary osteosynthesis, but they raise positioning difficulties (passage through the pad in particular).

Use can also be made of pins which have a smaller size. However, the stability obtained is unsatisfactory and it is necessary to withdraw them.

Intramedullary nails are also known, but they require supplementary stapling in order to prevent the bone parts to be joined from rotating relative to each other.

OBJECT OF THE INVENTION

It is the object of the invention to remedy these drawbacks simply, safely, effectively and efficiently.

The problem that the invention proposes to solve is to permit the fixation of two bone parts to one another, rigidly with dynamic and retentive compression, in order to obtain a reliable and rapid osteosynthesis.

SUMMARY OF THE INVENTION

To solve such a problem, an intramedullary arthrodesis element has been designed and developed which consists of a body with an elongated shape having, in succession, from one of its ends, a fixation zone cooperating with one of the bone parts to be immobilized, a median zone suitable for withstanding shear and bending stresses, and a fixation zone in the other bone part to be immobilized, each of the fixation zones being profiled and made from a material suitable for enabling introduction into the bone parts without a finger- or toe-tip approach, followed by a fixation in the bone parts, while avoiding any rotational movement, withstanding the tensile stresses, and maintaining a compressive force.

The invention has a particularly advantageous application, which can however not be considered as limiting, for the preparation of arthrodesis in the proximal and median phalanges, for proximal interphalangeal joints and distal interphalangeal joints, in the hand or foot.

To solve the problem of taking account of the anatomy, and particularly of the internal shrinkage of the bone, the median zone is linked to at least one of the fixation zones by a connecting zone.

To solve the problem of permitting implantation of the element followed by compression of the bone fragments, the fixation zones are made from a shape-memory material to be deformed by thermal and/or mechanical action.

To produce the fixation zones, which may be identical or not, various technical solutions are feasible, according in particular to the type of arthrodesis performed and the joints to be treated.

For example:
  one of the fixation zones has two tabs or wings separable under the action of the shape memory;
  one of the fixation zones has a tab or rod which can be curved under the action of the shape memory;
  one of the fixation zones has, in its thickness, a slot for permitting deformation by elasticity, or memory, under the action of the shape memory.

In one embodiment, the overall body has a flat cross-section.

BRIEF DESCRIPTION OF THE DRAWING

The invention is described below in greater detail in conjunction with the figures of the drawings appended hereto in which:

FIG. 1 is a schematic plan view showing the placement of the intramedullary arthrodesis element of the invention between a proximal phalange and a median phalange to consolidate the proximal interphalangeal joint;

FIG. 2 is a plan view of an embodiment of the arthrodesis element at the time of its introduction;

FIG. 3 is a view corresponding to FIG. 2 showing the arthrodesis element after its implant to produce the compression;

SPECIFIC DESCRIPTION

Figure 4:
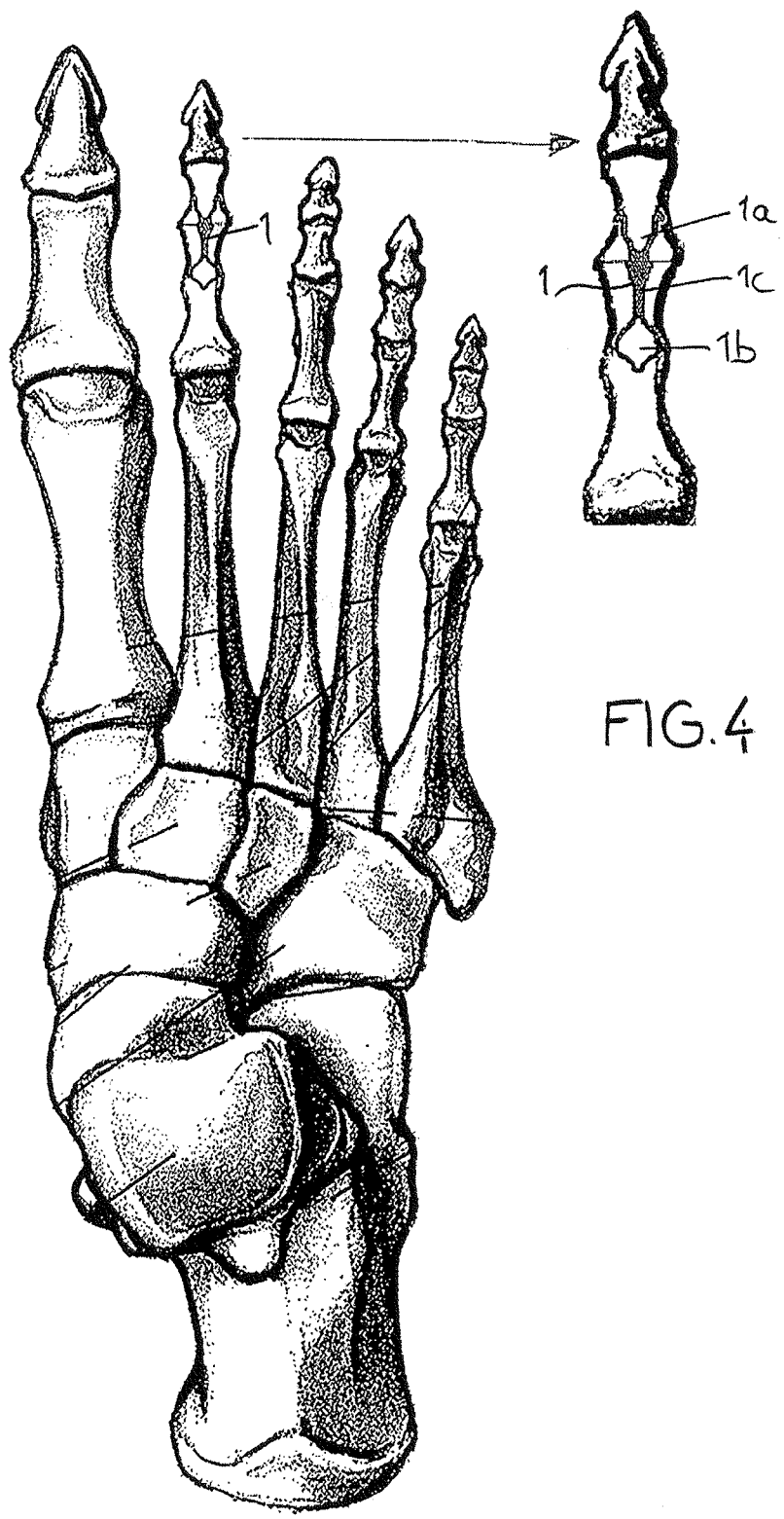
FIG. 4 shows the placement of the element of the invention in a toe.

The arthrodesis element of the invention consists of an elongated body 1. Each of the ends of the body 1 is conformed to produce a fixation zone 1a linked to a fixation zone 1b.

Between the two fixation zones 1a and 1b, at least one median zone 1c is formed capable of withstanding shear and bending stresses. In general, the shear and bending stresses are applied to the bone site to be consolidated. The shape of this median zone 1c is adapted to the internal shape of the bone. Its length is determined in order to allow a slight offset in the centering.

For information, and in a non-limiting manner, this median zone may have a rectangular cross-section measuring about 2 to 3 mm*1 to 1.5 mm and a length of about 3 to 5 mm for the foot and the hand.

The fixation zones 1a and 1b are conformed to prevent any rotational movement, resist tension, and maintain manual compression applied at the time of the implant by the surgeon in order to reduce the site. To obtain this result, the fixation zones 1a and 1b are made from a shape-memory material to be deformed by thermal action (tepid memory) or mechanical action (superelasticity) (see U.S. Pat. No. 5,958,159). The goal, in the fixation zones, considering their profile on the one hand and the type of material on the other, is to permit an introduction into the bone parts, particularly dorsally without a finger- or toe-tip approach, on the one hand, and to produce a fixation in the bone portion in order to obtain or to maintain the desired compressive force, on the other. The fixation zones 1a and 1b are identical or not, according to the type of bone and its morphology.

Depending on the type of arthrodesis performed, that is, the type of interphalangeal joint to be consolidated for example, the fixation zones 1a and 1b may have different embodiments.

For example, one of the fixation zones 1a has two tabs or wings that are separable under a thermal action for example. Otherwise, these fixation zones 1a may have a single tab or rod which can be curved under the action of a memory of the component material. Otherwise, the fixation zone 1b has, in its thickness, a slot to permit deformation by elasticity, under thermal action for example, and to maintain the position by pressing on the length of the bone.

According to another feature of the invention, to take account of the anatomy of the various phalanges for example, that is the internal shrinkage of the bone (hourglass shape), the median zone 1c is linked to at least one of the fixation zones 1b by a thinner connecting zone 1d.

Reference can be made to the figures of the drawings which show an embodiment of an intramedullar arthrodesis element.

In this embodiment, the body 1 has, at one of its ends, a fixation zone 1a in the form of two tabs or wings 1a1 1a2. This fixation zone 1a is prolonged by a median zone 1c of generally substantially triangular shape in a plan view. The median zone 1c is connected to the other end fixation zone 1b by a connecting zone 1d having a generally rectangular shape in a plan view. The fixation zone 1b has, in its thickness, a slot of generally oblong shape 1b1.

Reference can be made to FIG. 2 which shows the element at the time of its introduction, that is before separation of the tabs 1a1 and 1a2, and the opening of the slot 1b1. For example, this configuration is obtained when the overall element is subject to a temperature much lower than that of the human body for example. Conversely, after implantation (FIG. 3), under the effect of body heat, the tabs 1a1 and 1a2 separate, in the same way as the slot 1b1, concomitantly causing a deformation of the fixation zone 1b.

It should be noted that the profile of the median zone 1c prevents penetration when the site is reclosed.

In an alternative embodiment, the connecting zone 1d can be split to benefit from a swelling effect by shape memory and strengthening of the anchoring in the diaphyseal zone.

It should be recalled that the inventive element is ideal for the treatment of the hammer- or claw-toe syndrome, by performing an arthrodesis in the phalanges P1 and P2 on the radii 2 to 5, while observing that such applications must not be considered as limiting, by means of essentially dimensional adjustments (finger reimplants, arthrodesis of the distal interphalangeal joint and of the proximal interphalangeal joint of the hand, and the arthrodesis of the big toe).

Obviously, the entire arthrodesis element of the invention may have constructive features suitable for improving the fixation and compression in particular.

For example:
notches on the tabs on one of the sides for better fixation in the ethmoid bone;
wavy tabs implanted (straight before implant) to permit shortening and hence an additional compression of the arthrodesis site compared with a simple fixation;
a tapered central zone to avoid undesirable penetration of the implant at the time when the site is to be closed.

For information, the memory used is preferably a tepid memory, so that heating is unnecessary because of the lack of access. The opening begins at above 15 to 20° C. and stops at about 30 to 35° C.

The operating technique remains conventional.

The invention claimed is:

1. An intramedullary implant for use between a pair of adjacent bone parts, the implant extending along an axis and being unitarily formed, the implant comprising:
a generally triangular median zone having axially opposite ends and having a pair of side faces converging from one end toward an opposite end to form an abutment, the abutment having a width, said abutment adapted to be positioned against a surface of one of the bone parts;
two fixation zones made from a shape-memory material, each fixation zone including a
respective pair of tabs projecting longitudinally outward and away from each of the ends, the tabs of each pair being displaceable between an outer position in which they are widely spaced and diverge from each other axially away from the median zone and an inner position in which they are closely spaced, wherein the pairs of tabs made from shape-memory material assume the outer position at body temperature through shape-memory action,
wherein one of the pairs of tabs projects longitudinally outward and away from an end of the median zone forming the abutment, and has a width adjacent to the abutment, such that the width of the pair of tabs projecting from the end forming the abutment is less than the width of the abutment.

2. The intramedullary implant defined in claim 1, wherein the tabs are of wavy shape.

3. The intramedullary implant defined in claim 1, wherein the implant is further unitarily formed to include a connecting zone of predetermined length between the median zone and one of the pairs of tabs.

4. The intramedullary implant defined in claim 3, wherein the connecting zone is of generally rectangular shape and has a pair of side faces extending substantially parallel to the axis.

5. The intramedullary implant defined in claim 3, wherein both the median and connecting zones are substantially planar.

6. The intramedullary implant device defined in claim 1, wherein the entire device is made of shape-memory material.

7. The intramedullary implant device defined in claim 1, wherein the median zone is flat and lies generally in a plane in which the tabs also generally lie.

8. The intramedullary implant device defined in claim 1, wherein at least two of the tabs have outer ends formed with outwardly projecting barbs.

9. The intramedullary implant device defined in claim 1, wherein at least two of the tabs have outer ends that are joined unitarily together such that they form an O-shape in the outer position.

10. The intramedullary implant device defined in claim 1, wherein the tabs of one end project outward in a V-shape.

11. The intramedullary implant device defined in claim 1, wherein the length of the median zone is between 3 mm and 5 mm.

12. An intramedullary implant device for implantation at an arthrodesis site between a pair of adjacent bone parts, the device being unitarily formed and comprising:
   a central part having a predetermined length of between 3 mm and 5 mm in order to allow a slight centering offset and longitudinally opposite ends; and
   respective pairs of tabs projecting longitudinally outward and away from each of the ends, the tabs of each pair being displaceable between an outer position in which they are widely spaced and diverge from each other away from the central part and an inner position in which they are closely spaced, wherein the tabs of each pair are constructed of a shape-memory material and assume the outer position at body temperature through shape-memory action, the tabs at one of the ends having outer end portions joined unitarily together, the portions being arcuate and convex toward each other to permit shortening and compression of the arthrodesis site.

13. The intramedullary implant device defined in claim 12, wherein the central part has a triangular median zone that forms at one end an outer face extending generally perpendicular to the axis.

14. The intramedullary implant device defined in claim 13, wherein the central part is further unitarily formed to include a connecting zone of predetermined length between the median zone and one of the pairs of tabs.

15. The intramedullary implant device defined in claim 14, wherein the connecting zone is of generally rectangular shape and has a pair of side faces extending substantially parallel to the axis.

16. The intramedullary implant device defined in claim 14, wherein both the median and connecting zones are substantially planar.

17. The intramedullary implant device defined in claim 12, wherein the entire device is made of shape-memory material.

18. The intramedullary implant device defined in claim 12, wherein the central part is flat and lies generally in a plane in which the tabs also generally lie.

19. The intramedullary implant device defined in claim 12, wherein at least two of the tabs have outer ends formed with outwardly projecting barbs.

20. The intramedullary implant device defined in claim 12, wherein at least two of the tabs have outer ends that are joined unitarily together such that they form an O-shape in the outer position.

21. An intramedullary implant device for implantation between a pair of adjacent bone parts, the device being unitarily formed of flat cross section, the implant comprising:
   a central part having longitudinally opposite ends;
   a first fixation zone having a respective pair of first tabs projecting longitudinally away from one of the ends, the first tabs being displaceable between an outer position in which they are widely spaced and diverge from each other away from the central part and an inner position in which they are closely spaced, wherein the tabs of the first fixation zone are constructed of a shape-memory material and the tabs of the first fixation zone assume the outer position at body temperature through shape-memory action; and
   a second fixation zone projecting outward and away from the other end and having a second pair of tabs constructed of a shape-memory material and having outer ends that are joined unitarily together such that they form a throughgoing planar slot permitting transverse expansion by shape-memory action at body temperature.

22. An intramedullary implant for use between a pair of adjacent bone parts, the implant extending along an axis and being unitarily formed, the implant comprising:
   a generally triangular median zone having axially opposite ends one of which forms an outer face extending generally perpendicular to the axis to form an abutment having a width, the abutment being adapted to be positioned against a surface of one of the bone parts;
   two fixation zones made from a shape-memory material;
   each one of the fixation zones having a respective pair of tabs projecting longitudinally outward, each pair of tabs being displaceable between an outer position in which they are widely spaced and diverge from each other axially away from the median zone and an inner position in which they are closely spaced, wherein the pairs of tabs assume the outer position by shape-memory action at body temperature; and
   a connecting zone between the median zone and a fixation zone and extending over a predetermined length, wherein the connecting zone has a width that is less than the width of the abutment.

23. The intramedullary implant device of claim 21, further comprising a connecting zone between a median zone and the second fixation zone and extending over a predetermined length, wherein the connecting zone provides a slight centering offset of the first and second fixation zones relative to the pair of adjacent bone parts.

24. The intramedullary implant of claim 22, wherein one of the pairs of tabs projects longitudinally outward from the outer face of the abutment and the outer face of the abutment extends further from the axis than a width of the pair that projects longitudinally outwardly from the outer face.

* * * * *

UNITED STATES PATENT AND TRADEMARK OFFICE
CERTIFICATE OF CORRECTION

PATENT NO.        : 8,475,456 B2                                                      Page 1 of 1
APPLICATION NO.   : 11/911405
DATED             : July 2, 2013
INVENTOR(S)       : Marc Augoyard et al.

It is certified that error appears in the above-identified patent and that said Letters Patent is hereby corrected as shown below:

In the Claims

Col. 5, Line 21, before "compression" insert -- enhance --.

Signed and Sealed this
Twelfth Day of May, 2015

Michelle K. Lee
*Director of the United States Patent and Trademark Office*